United States Patent [19]

Bateman et al.

[11] Patent Number: 4,980,403

[45] Date of Patent: Dec. 25, 1990

[54] COLLAGEN PRODUCTS

[75] Inventors: John F. Bateman, Balwyn; John A. M. Ramshaw, Brunswick; David E. Peters, Wonga Park; Peter A. Tulloch, Parkville, all of Australia

[73] Assignee: The University of Melbourne, Victoria, Australia

[21] Appl. No.: 127,661

[22] PCT Filed: Jan. 2, 1987

[86] PCT No.: PCT/AU87/00001

§ 371 Date: Nov. 5, 1987

§ 102(e) Date: Nov. 5, 1987

[87] PCT Pub. No.: WO87/04078

PCT Pub. Date: Jul. 16, 1987

[30] Foreign Application Priority Data

Jan. 6, 1986 [AU] Australia .................... PH4101

[51] Int. Cl.$^5$ .................... C08J 3114; C08L 89/06; C07K 15/06; A61K 37/00
[52] U.S. Cl. .................... 524/17; 524/21; 524/22; 424/94.2; 514/21; 530/355; 530/356; 530/840; 530/842
[58] Field of Search .................... 424/94.2; 514/21; 530/356, 355, 840, 842; 524/17, 21, 22

[56] References Cited

U.S. PATENT DOCUMENTS

| | | | |
|---|---|---|---|
| 3,630,840 | 12/1971 | Wagner et al. | 530/421 |
| 3,770,631 | 11/1973 | Fekete et al. | 210/732 |
| 3,883,448 | 5/1975 | Sternberg | 530/421 |
| 4,488,911 | 12/1984 | Luck et al. | 530/842 |
| 4,645,829 | 2/1987 | Ho | 530/344 |

OTHER PUBLICATIONS

Leibovich and Weiss, *Biochem. Biophys. Acta.*, 214: 445–454, 1970.

Lee and Pez, *Collagen Rol. Res.*, 3/2: 89–103, 1983.

*Primary Examiner*—Merrell C. Cashion, Jr.
*Assistant Examiner*—Carlos Azpuru
*Attorney, Agent, or Firm*—Scully, Scott, Murphy & Presser

[57] ABSTRACT

Collagen in tactoid form obtained by forming an aqueous solution containing dissolved collagen and a water soluble or miscible polymer adapted to precipitate collagen out of solution in the form of tactoids.

18 Claims, No Drawings

COLLAGEN PRODUCTS

This invention relates to collagen products.

In a particular aspect this invention relates to collagen products made from soluble collagen. A new method by which soluble collagen can be formed into quasi-crystalline structures by precipitation using soluble polymers is described. The use of an aggregate of this quasi-crystalline collagen to form a variety of collagen materials which have improved properties compared with existing collagenous materials is described. Such improved collagen materials have application in various fields including the manufactures, for example, of products for medical use.

Collagen is an extremely common protein in the animal kingdom and therefore many uses for products based upon collagen have developed. Many products use collagen in either its native form (i.e. the triple helical structure pre-existing in an animal or human body), or regenerated into this form, or after denaturation of the collagen, in the form of gelatine. Native collagen is used for various products such as in the production of leather from animal skins, or such as the production of sausage casings in which the collagen is finely divided and reformed into the desired structure.

There are also many uses of collagen and for items made from collagen in medical fields such as in artificial arteries, veins, tendons, corneas, heart valves, skin, or patches or the like which are used as replacement parts for disease or injury affected parts in humans, or in cosmetic applications such as mammary prostheses or injectable collagen, or in collagen sponges, sutures or haemostat materials which may be used during surgery or in the treatment of disease (Chvapil, 1979). Many of these medical products made from collagen are at present unsatisfactory because of an inability to reproduce the native structure, composition or strength which exists in the normal collagenous tissue or because of the immune response elicited by the presence of immunogenic collagen or components or other material foreign to the body.

In its native form in the body, collagen exists in many types and in the most common of these types, collagen exists as fibrils in which individual collagen molecules are arranged in a staggered overlap structure (Bornstein and Traub, 1979). These fibrils are stabilised and made insoluble by intermolecular crosslinks between the non-helical portions (telopeptides) of adjacent collagen molecules (Bornstein and Traub, 1979). If the collagen, from normal, mature tissue is to be made soluble the crosslinks must be broken, for example by digestion with an enzyme such as pepsin.

Soluble collagen can be reconstituted in a variety of ordered aggregate forms. Some are fibrous in form, and fibrils in which the collagen is arranged in its native staggered way can be reformed. The rate of the fibril reforming process is enhanced if collagen with intact telopeptides is used. However, results from the use of injectable soluble collagen have shown that the telopeptides lead to an antigenic response in humans; collagen lacking telopeptides is relatively non antigenic (Linsenmayer, 1982) but can still be made to form fibrils. Materials formed by fibril regeneration are often too hydrated and additional methods such as freezedrying or cell-induced contraction must be used to give a functional product.

Other non-native fibrous aggregates, termed FLS collagen, can be formed in which the collagen molecules are arranged in various staggered arrangements with the orientation of the molecules in both directions.

Quasi-crystalline aggregates can also be formed. These include very small crystallites of collagen, termed SLS collagen, in which the collagen molecules all have the same orientation, but there is no stagger between molecules. These have been of partial use in deducing the native structure of collagen but SLS collagen has been of little use in the manufacture of larger structures like biomedical products. Also, quasi-crystalline tactoids of collagen can be prepared, using conditions similar to those used for reconstituting fibrils, by heat gelation (Leibovich and Weiss, 1970; Lee and Piez, 1983) but the technique of production is more difficult than the technique described here as it does not involve simple precipitation. In these structures the collagen is arranged in a staggered form similar to native fibrils. In the present work the tactoids are produced by a new procedure, precipitation by soluble, neutral polymers. When collagen is precipitated by other procedures, for example salts, alcohols or heat, amorphous precipitates are formed.

DESCRIPTION OF THE INVENTION

During a search for more efficient methods of isolating soluble collagen it was found that the addition of water soluble polymers to a solution of collagen resulted in an efficient precipitation of the collagen from solution and the precipitated collagen was found to be much easier to separate from the liquid phase than with precipitates of collagen formed by the use of salts, alcohol or heat. The polymers had other advantages when compared with these previously used precipitants including that they were non-denaturing and did not require removal prior to chromatography or electrophoresis.

It was an unexpected finding that the collagen had precipitated in the form of small, needlelike, quasi-crystalline tactoids which were visible under the light microscope.

It was a further unexpected discovery that the tactoids could be induced to form into larger assemblages either by allowing the suspension to mature for a period of time or by mechanical action, and that the tactoids or their assemblages could be formed into shapes.

Accordingly, the present invention provides a method of producing a collagen product comprising forming an aqueous solution containing dissolved collagen and a water soluble or miscible polymer adapted to precipitate the collagen out of solution in the form of tactoids.

The pH of the said solution is preferably 3.5-10 more preferably 5-8 with 7-8 being still more preferred and about 7.5 being most preferred.

The collagen precipitate may be left in the form of a paste or slurry and used in this form or after concentration by any one of the methods gravitational precipitation, filtration, centrifugation or the like. The precipitate may be crosslinked, tanned or stabilized by one or more of chemical, physical or biochemical methods either before or after it has been concentrated. Crosslinking, tanning or stabilisation applied to the precipitate before concentration makes the tactoids resistant to deforming actions such as heating, pressure or biochemical degradation. Crosslinking, tanning or stabilisation applied to the precipitate after concentration causes the structure formed during the concentration process to become more stable.

The so precipitated collagen may also be formed, for example, into a synthetic body part. Such forming into a synthetic body part may be effected by gravitational precipitation, filtration, centrifugation, moulding, pressing, shaping or any other way of combination of ways.

Shapes which may be prepared include sheets, tubes, strings and rods.

It has been found particularly desirable to form the so precipitated collagen into sheets for use as synthetic dressings for wounds and into tubes for use as synthetic tubular body parts. The sheets can be formed by centrifugation in a large basket centrifuge or the like or by gravitational precipitation or filtration. Other methods of producing the sheets are also possible. A more compacted sheet is produced by centrifugation in comparison with gravitational precipitation or filtration. Tubes can also be prepared by centrifugation or by casting, moulding or shaping.

The collagen may be precipitated onto a suitable substrate to form a composite material. Such a substrate, onto which the collagen is precipitated, may have the form of a particular body part or biomedical product.

The substrate may take the form of a matrix.

The substrate may take the form of a plastic or other synthetic surface in the form of a sheet, tube or mesh, onto which the collagen is directly deposited forming a collagenous coating.

The substrate may also take the form of a composite, for example, various synthetic layers bonded to an artificially or naturally-produced matrix.

These collagen coated substrates may also be chemically modified. For example, glutaraldehyde or similar chemicals may be used to stabilize the matrix.

The collagen of the present invention may be used as a paste or slurry. Such a paste or slurry would have a number of applications including as an implant material such as in the form of an injectable medium for use in cosmetic surgery. Such a slurry may be stabilized chemically such as by glutaraldehyde or irradiation. Such as with gamma radiation. The concentration of this tactoidal collagen in the paste or slurry is preferably not less than 10 mgm/ml, more preferably not less than 30 mgm/ml and most preferably not less than 40 mgm/ml.

The collagen useful for forming the collagen products of this invention includes collagen derived from hides, skins or other collagen containing organs or tissues of humans or other vertebrates or invertebrates and includes collagens of one type or mixtures of types. Soluble collagen can be prepared by enzymic treatment of collagen from those sources. Suitable enzymes include pepsin.

The collagen may also be derived from the culture medium of cells, tissues or organs grown in cell- or tissue-culture. The culture medium used to produce the collagen may be a culture medium from cell or tissue culture derived from a person for whom a synthetic body part is to be produced; it is believed that doing this will substantially reduce the likelihood of rejection. Further, it is also possible that a substrate may be introduced into the culture medium such that collagen and other components will be directly produced thereon. Such a substrate may have the form of a particular body part or biomedical product desired. The substrate may take the form of a matrix. The substrate may take the form of a plastic or other synthetic surface in the form of a sheet, tube or mesh, onto which the collagen and other components are directly deposited forming a collagenous coating. The substrate may be formed from aggregates of tactoidal collagen of this invention.

The water soluble or miscible polymer is preferably a neutral polymer. Such polymers may be at least one of the synthetic polymers polyvinyl alcohol, polyethylene oxide, polyvinylpyrrolidinone, polyacrylamide, polyethylene glycol, polypropylene glycol, polyvinyl methyl ether, maleic anhydride copolymers and the like; or at least one of the modified, natural, neutral polymers hydroxyethyl starches, methyl cellulose, hydroxymethyl cellulose, hydroxyethyl cellulose, hydroxypropyl cellulose or the like; or at least one of the natural neutral polymers agarose, dextrins, dextrans, starches, pectins, alginates and the like. Mixtures of such polymers may be used and the molecular weight of the polymer or polymers can vary over a wide range provided the polymer remains soluble or miscible with water.

This list of polymers is not exhaustive as the important factor is the use of a water soluble polymer or polymers to precipitate the collagen. Neutral water soluble or miscible polymers are preferable but charged, water soluble polymers may also be used particularly if they are only mildly charged.

The precipitate of collagen is generally found to be improved if it is allowed to stand in said solution. Such standing is preferable for a period of one hour to six months with one day to one month being more preferred.

Such standing is effected at temperatures between the denaturation temperature of the collagen and the freezing point of the solution; preferably at between zero and 20° C.; more preferably between zero and 10° C.

If desired, added materials such as plasticisers, colourants, biologically active materials such as proteoglycans or glycosaminoglycans, proteins, other extracellular products, hormones, growth factors, antibiotics and agents which affect wound healing or have other beneficial effects, ionic strength modifiers such as salts, or solids such as insoluble collagen or the like may be included with the so precipitated collagen and incorporated into material made from the collagen. These added materials may also be incorporated into the solution of soluble collagen before addition of the polymer or otherwise incorporated into material made from the collagen. Charged, water soluble or water miscible polymers may be used as part of a mixture with the neutral polymer or polymers and added to the soluble collagen with the neutral polymer solution. These charged polymers may be used to modify the properties of the soluble collagen solution or the material made from the precipitated collagen.

The collagen product of this invention may be chemically or biochemically stabilised. Biochemical stabilisation may be effected by enzymes such as lysyl oxidase. Chemical stabilisation may be effected by tanning agents, syntans, other cross-linking agents or chemical modifiers of collagen. Of particular interest are stabilisers which limit proteolysis or the immunogenicity of the collagen. Glutaraldehyde is a stabiliser of particular interest. The product may also be stabilised by dehydration by mild heat, water miscible solvents, critical point drying or the like. Such stabilisation may be performed before or after a shaping operation. The collagen product of this invention may be sterilised chemically or by irradiation. Chemical sterilisation may be conducted by means of suitable solutions of sterilising materials such as glutaraldehyde from between 0.5% to 5% concentration. The product may be stored in solutions of sterilant until required for use. Sterilisation by means of irradiation can be conducted by exposing the collagen product of this invention to gamma rays from a suitable source. From 0.5 to 5 Mrads of irradiation may be used, preferably 2.5 Mrads of gamma ray irradiation is suitable for satisfactory sterilisation of the product.

The tactoids formed by precipitation of the soluble collagen in this invention are useful in production of synthetic body parts, and other materials for medical or veterinary applications. The collagen tactoids or tactoid assemblages could be stabilised by chemical or biochemical techniques or could be formed into various useful shapes and then stabilised. The tactoidal collagen has potential application in many areas such as the manufacture of collagen sponges or haemostatic agents, of dressings, of membranes, of skin, of tubes and the like and in the treatment of disease such as peridontal disease. The tactoidal collagen can also be used in conjunction with other structural type materials to form composite materials with different properties. For example, a tube of tactoidal collagen can be covered with a woven or knitted mesh of fibre such as Dacron to give the tube additional strength. Alternatively, the tactoidal collagen can be formed into a tube surrounding the mesh to give a more intimate contact with the mesh and better properties. To better utilise the properties of the tactoidal collagen in the formation of artificial body parts it is possible to arrange the tactoids in a preferred orientation by the application of an electric field or by means of mechanical action. Materials made from the oriented tactoids may have beneficial effects in the healing of wounds. Many other methods of utilising the tactoidal collagen in a variety of shapes and forms and in conjunction with diverse other materials can be envisaged.

The product of this invention also has application in areas outside medical and veterinary products including plastics, fabric, leather or as composites or the like.

The present invention also includes such collagen products and articles produced therefrom.

The collagen products of this invention have advantages over presently available products. These include, low immunogenicity, ease of preparation, high collagen content, and strength.

The following examples illustrate the invention.

EXAMPLE 1

Type I collagen was solubilised and extracted from foetal calfskin by pepsin digestion and purified by fractional salt precipitation according to the method of Trelstad et al. (1967). This purified collagen was dissolved in 200 mM Tris-HCl buffer pH 7.5 at 4° C. and at a concentration of 10 mg/ml. Polyethylene glycol (PEG) 4000 was then added to produce a final concentration of 2.5% (w/v). A precipitate of tactoidal collagen formed which settled to the bottom of the container after standing at 4° C. for a few hours or could be concentrated by filtration or centrifugation.

EXAMPLE 2

As for Example 1 except that the concentration of the collagen was 1 mg/ml.

EXAMPLE 3

As for Example 2 except that PEG 400 to a final concentration of 3.5% (w/v) was used to precipitate the collagen.

EXAMPLE 4

Type III collagen, solubilised and extracted as in Example 1, was dissolved at a concentration of 1 mg/ml in 200 mM Tris-HCl buffer pH 7.6 at 4° C. PEG 400 was added to the solution to a final concentration of 4.0% (w/v) and the precipitate of tactoidal collagen formed.

EXAMPLE 5

As for Example 4 except that a final concentration of 2.5% (w/v) PEG 4000 was used.

EXAMPLE 6

Type II collagen was isolated by the method of Trelstad et al. (1976) from bovine articular cartilage by pepsin solubilisation and fractional salt precipitation. The purified type II collagen was dissolved in 200 mM Tris-HCl buffer at pH 7.6 at 4° C. and at a concentration of 1 mg/ml. PEG 400 was then added to produce a final concentration of 3.0% (w/v). The precipitate of tactoidal collagen formed as in Examples above.

EXAMPLE 7

As for Example 6 except that PEG 4000 was added to a final concentration of 2.0% (w/v).

EXAMPLE 8

As for Example 1 except that PEG 1000 to a final concentration of 5% (w/v) was used to precipitate the collagen.

EXAMPLE 9

As for Example 1 except that PEG 10000 to a final concentration of 5% (w/v) was used to precipitate the collagen.

EXAMPLE 10

The suspension of tactoidal collagen from Example 1 was stored at 4° C. for 4 weeks and collected on Whatman No. 1 filter paper in a 125 mm diameter basket centrifuge rotating at 4000 rpm. The resulting collagen sheet was removed from the centrifuge and separated from the filter paper. The collagen sheet was found to have properties similar to those of a thick, wet paper tissue and to be suitable for assisting in the healing of open skin wounds.

EXAMPLE 11

The collagen sheet, prepared as in Example 10, was tanned using a solution of 0.01% glutaraldehyde for 18 hours. After drying the sheet was found to have a tensile strength of 6.2 N/sq cm and an elongation of 12% at a moisture content of 16%.

EXAMPLE 12

The collagen sheet, prepared as in Example 10 was sealed in a polyethylene bag and subjected to 2.5 Mrads of gamma ray irradiation. The sheet was found to have been sterilised and to have improved tensile properties over those of the sheet in Example 10.

EXAMPLE 13

As for Example 2 except that the buffer was at pH 5.

EXAMPLE 14

As for Example 1 except that the collagen extracted from foetal calfskin was not purified by fraction salt precipitation but was used as a crude extract and that 5% PEG 4000 was used.

EXAMPLE 15

As for Example 14 except that 5% polyvinyl alcohol was used.

EXAMPLE 16

As for Example 14 except that 5% dextran of 10,000 average molecular weight was used.

EXAMPLE 17

As for Example 14 except that 5% dextran of 40,000 average molecular weight was used.

EXAMPLE 18

A collagen sheet prepared as in Example 10 was rolled into a tube and then stabilized by tanning using a solution of 0.01% glutaraldehyde for 18 hours.

EXAMPLE 19

A collagen sheet prepared as in Example 10 was dried by critical point drying using liquid carbon dioxide.

BIBLIOGRAPHY

Chvapil, M. (1979)—In "Fibrous Proteins, Scientific, Industrial and Medical Aspects", Vol. 1 (Eds Parry, D. A. D and Creamer L. K.) Academic Press, London pp 247–269. Bornstein, P. and Traub, W. (1979) In "The Proteins" Vol 4 (Eds Neurath, H. and Hill, R. L.) Academic Press, New York pp 411–632.

Linsenmeyer, T. F. (1982) In "Collagen in Health and Disease" (Eds Weiss, J. B. and Jayson, M. I. V.) Churchill Livingston, Edinburgh pp 244–268.

Leibovich, S. J. and Weiss, J. B. (1970) Biochim. Biophys. Acta 214:445–465. Electron microscope studies of the effects of endo- and exo-peptidase digestion on tropocollagen.

Lee, S. L. and Piez, K. A. (1983) Collagen Rel. Res. 3:98–103. Type II collagen from Lathyritic rat chondrosarcoma: preparation and in vitro fibril formation.

Trelstad, R. L., Catanese, V. M. and Rubin, D. F. (1976) Anal. Biochem. 71:114–118. Collagen fractionation: Separation of native types I, II and III by differential precipitation.

Modifications and adaptations may be made to the above described without departing from the spirit and scope of this invention which includes every novel feature and combination of features disclosed herein.

We claim:

1. A method of producing a collagen product comprising forming an aqueous solution containing dissolved collagen, said solution having a pH of from about 3.5 to about 10, and adding a water soluble or miscible uncharged, neutral polymer to said solution in a concentration sufficient to cause precipitation of said collagen out of said solution in the form of tactoids, said method carried out at a temperature in the range of between the denaturation temperature of the collagen and the freezing point of the solution.

2. A method of producing a collagen product as claimed in claim 1, wherein the pH of said solution is 7–8.

3. A method of producing a collagen product as claimed in claim 2, including forming the thus formed precipitate to a shape.

4. A method of producing a collagen product as claimed in claim 3, including precipitating the collagen onto a pre-shaped substrate.

5. A method of producing a collagen product as claimed in claim 4, wherein the substrate has the form of a body part.

6. A method of producing a collagen product as claimed in claim 4, wherein the substrate is itself formed of collagen in the form of tactoids.

7. A method of producing a collagen product as claimed in claim 3, wherein prior into forming said precipitate to a shape the precipitate is permitted to stand in said solution for a period of greater than 1 hour.

8. A method of producing a collagen product as claimed in claim 2 wherein the temperature of carrying out the method is from about 0° C.

9. A method of producing a collagen product as claimed in claim 1, and including the step of chemically or biochemically stabilizing the collagen so formed.

10. A method of producing a collagen product as claimed in claim 1, wherein the dissolved collagen is derived from cell or tissue culturing.

11. A method of producing a collagen product as claimed in claim 2, wherein said water soluble or miscible polymer is selected from the group consisting of polyvinyl alcohol, polyethylene oxide, polyvinylpyrrolidinone, polyacrylamide, polyethylene glycol, polypropylene glycol, polyvinyl methyl ether and maleic anhydride copolymers.

12. A method of producing a collagen product as claimed in claim 2, wherein said water soluble or miscible polymer is selected from the group consisting of hydroxyethyl starches, methyl-cellulose, hydroxymethyl cellulose, hydroxyethyl cellulose and hydroxypropyl cellulose.

13. A method of producing a collagen product as claimed in claim 2, wherein said water soluble or miscible polymer is selected from the group consisting of agarose, dextrins, dextrans, starches and pectins.

14. A collagen product formed by the method of any one of claims 2, 8, 11, 12 or 13.

15. A collagen product as claimed in claim 14 in admixture with a biologically active material, selected from the group consisting essentially of proteoglycans, glycosaminoglycans, proteins, extracellular products, hormones, growth factors, antibiotics and wound-healing agents, insoluble collagen or a derivative thereof, and ionic strength modifiers.

16. A collagen product as claimed in claim 14 in the form of a sheet or a tube.

17. A collagen product as claimed in claim 14 in the form of a slurry or a paste.

18. A collagen product as claimed in claim 17 wherein said collagen is present in a concentration of at least 10 mgm/ml.

* * * * *

UNITED STATES PATENT AND TRADEMARK OFFICE
CERTIFICATE OF CORRECTION

PATENT NO. : 4,980,403

DATED : December 25, 1990

INVENTOR(S) : John F. Bateman, et al.

It is certified that error appears in the above-identified patent and that said Letters Patent is hereby corrected as shown below:

Column 8, line 7, Claim 3: "2" should read as --1--

Column 8, line 24, Claim 8: "0° C." should read as --0° C to about 20° C.--

Column 8, line 32, Claim 11: "2" should read as --1--

Column 8, line 39, Claim 12: "2" should read as --1--

Column 8, line 45, Claim 13: "2" should read as --1--

Column 8, line 49, Claim 14: "2" should read as --1--

Signed and Sealed this

Fifth Day of May, 1992

*Attest:*

DOUGLAS B. COMER

*Attesting Officer*  *Acting Commissioner of Patents and Trademarks*